US006410024B1

(12) United States Patent
Burnie et al.

(10) Patent No.: US 6,410,024 B1
(45) Date of Patent: Jun. 25, 2002

(54) EPITOPES OF SHIGELLA LIKE TOXIN AND THEIR USE AS VACCINE AND IN DIAGNOSIS

(75) Inventors: James Peter Burnie; Ruth Christine Matthews, both of Alderley Edge (GB)

(73) Assignee: NeuTech Pharma PLC, Manchester (GB)

( * ) Notice: Subject to any disclaimer, the term of this patent is extended or adjusted under 35 U.S.C. 154(b) by 0 days.

(21) Appl. No.: 09/463,129

(22) PCT Filed: Jul. 17, 1998

(86) PCT No.: PCT/GB98/02156

§ 371 (c)(1), (2), (4) Date: Jan. 20, 2000

(87) PCT Pub. No.: WO99/05169

PCT Pub. Date: Feb. 4, 1999

(30) Foreign Application Priority Data

Jul. 21, 1997 (GB) ............................................ 9715177

(51) Int. Cl.$^7$ ................................................ A61K 39/02

(52) U.S. Cl. ............................... 424/190.1; 424/236.1; 530/328

(58) Field of Search ........................... 424/190.1, 236.1; 530/93.2, 328, 350; 536/23.1; 435/7.1, 38; 436/518

(56) References Cited

U.S. PATENT DOCUMENTS

| | | | | | |
|---|---|---|---|---|---|
| 5,552,144 | A | * | 9/1996 | Samuel | 424/236.1 |
| 5,681,736 | A | * | 10/1997 | Pace et al. | 435/252.1 |
| 5,719,064 | A | * | 2/1998 | Scofield et al. | 436/518 |
| 5,858,352 | A | * | 1/1999 | Pace et al. | 424/93.4 |
| 5,955,293 | A | * | 9/1999 | Keusch et al. | 435/7.92 |
| 6,080,400 | A | * | 6/2000 | Williams et al. | 424/93.2 |

FOREIGN PATENT DOCUMENTS

| | | | |
|---|---|---|---|
| WO | 93/18784 | * | 9/1993 |
| WO | 96 30043 | | 10/1996 |
| WO | 98 11229 | | 3/1998 |

OTHER PUBLICATIONS

Haddad, JE et al, Journal of Bacteriology, vol. 175(16), pp. 4970–4978, Aug. 1993 (abstract only).*

Yamasaki, S et al, Microbial pathogenesis, Jul. 1991, vol. 11(1), pp. 1–9, (abstract only).*

Franke, S et al, Journal of Clinical Microbiology, vol. 33, pp. 3174–3178, (sequence alignment, abstract), 1995.*

Meyer, TH et al, Int. J. Med. Microbiology, Virol., Parasitol. Infect. Disease, vol. 276, pp. 176–188, (sequence alignment, abstract), 1992.*

Gomez, H et al, Pediatric Research, vol. 35(4part2), p. 180A, abstract only, May 1994.*

Perera, Liyanage Parakrama, Ph.D. thesis, vol. 51/09B of dissertation abstracts international, p. 4180, A structure–function analysis of shiga–like toxin type II of enterohemorrhagic *Escherichia coli*, 1990.*

Paton, AW et al, Journal of Clinical Microbiology, vol. 34(2), pp. 463–465, Feb. 1996.*

Paton, AW et al Microbial Pathogenesis, vol. 15, pp. 77–82, 1993.*

McEwen, J Immunological Letters, vol. 21(2), pp. 157–163, Expression of Shiga toxin epitopes in *Escherichia coli* immunological characterization, 1989.*

Karch, H et al, Zentralblatt fur Bakteriologie, Mikrobiologie und Hygiene, Nov. 1988, vol. 270 (1–2), pp. 41–51.*

Ryd, M et al, Microbial Pathogenesis, vol. 12(6), pp. 399–407, Jun. 1992.*

Boyd, B, Infection and Immunity, vol. 59(3), pp. 750–757, Mar. 1991.*

Levine, MM et al, Journal of Clinical Microbiology, vol. 30(7), pp. 1636–1641, Jul. 1992.*

Padhye, VV et al, Journal of Medical Microbiology, vol. 30(3), pp. 219–216, Nov. 1989, (abstract only).*

Jackson, MP et al, Journal of bacteriology, voo. 172(6), pp. 3346–3350, Jun. 1990, (abstract only).*

Deresiewicz, RL et al, Molecular and general genetic, vol. 241(3–4), pp. 467–473, Nov. 1993 (abstract only).*

Bast, et al: "Murine antibody responses to the verotoxin 1B subunit: demonstration of major histocompatibility complex dependence and an immunodominant epitope involving phenylalanine 30" Infect. Immun (1997), 65(7), 2978–2982 CODEN: INFIBR; ISSN: 0019–9567, 1997, XP002084527.

* cited by examiner

*Primary Examiner*—Lynette R. F. Smith
*Assistant Examiner*—Ginny Allen Portner
(74) *Attorney, Agent, or Firm*—Pillsbury Winthrop LLP

(57) ABSTRACT

The present invention concerns immunogenic epitopes of Shigella-like toxins (SLTs), particularly the Shigella-like toxin of *E. coli* 0157:H7, their use as immunogens and in treatment or diagnosis, agents (for example antibodies and antigen-binding fragments) which specifically neutralise them, their use in treatment and diagnosis, and methods for same.

6 Claims, No Drawings

EPITOPES OF SHIGELLA LIKE TOXIN AND THEIR USE AS VACCINE AND IN DIAGNOSIS

This application is the national phase of international application PCT/GB98/02156 filed Jul. 17, 1998 which designated the U.S.

The present invention concerns immunogenic epitopes of Shigella-like toxins (SLTs), particularly the Shigella-like toxin of *E. coli O*157:H7, their use as immunogens and in treatment or diagnosis, agents (for example antibodies and antigen-binding fragments) which specifically neutralise them, their use in treatment and diagnosis, and methods for same.

Shigella-like toxins (also known as Shiga-like toxins and Vero toxins) are well known (Schmitt, C. K. et al, 1991, Infection and Immunity, 59 (13): 1065–1073) and are produced by a wide range of pathogens including *E. coli O*157:H7, infection causing bloody diarrhoea and acute kidney failure, with many patients, particularly the young and elderly, failing to survive an infection. Outbreaks are sporadic but of significant size and present a substantial burden on health care resources (Berkelman, R. L. et al., 1994, Science, 264: 368–370; Slutsker, L. et al., 1997, Ann. Intern. Med., 126: 505–513). In the US alone, an estimated 20,000 cases of *E. coli O*157:H7 infection occur annually. Infection frequently occurs as a result of consuming contaminated foods, particularly ground beef products such as hamburgers, and by person-to-person contact in child care centres. Other reported outbreaks have occurred in Scotland and Japan (1996, BMJ, 313: 1424), the Pacific North West (Antibiotic-Resistant Bacteria, Office of Technology Assessment, Congress of the United States, pp 150–151) and Canada (Slutsker, L. et al., 1997, Ann. Intern. Med., 126: 506–513), although outbreaks are in no way limited to these regions.

Many of the infecting pathogens have acquired multiple drug resistance, and it has been found that antibiotic treatment may cause the bacteria to increase the production of the Shigella-like toxin (Antibiotic-Resistant Bacteria, supra). A need for novel therapeutics for pathogens expressing Shigella-like toxins has been felt for many years (see for example Antibiotic-Resistant Bacteria, supra). It has been suggested (Antibiotic-Resistant Bacteria, supra) that antibodies specific against the Shigella-like toxin of *E. coli O*157:H7 may have therapeutic potential, but to date antibodies have not been used therapeutically.

Various Shigella-like toxins have been cloned and sequenced (Meyer, T. et al., 1922, Zbl. Bakt., 276: 176–188, Schmitt, C. K. et al., 1991, Infection and Immunity, 59 (3): 1065–1073, Ramotar, K. et al., 1995, J Clin. Microbiol, 33 (3): 519–524). However, immunogenic regions, particularly specific epitopes of the toxins have not been identified.

The present inventors have now succeeded in identifying a number of epitopes from *E. coli* Shigella-like toxins, particularly those of *E. coli O*157:H7. The epitopes have a wide range of uses—they may be used therapeutically as immunogens, for example as vaccines, or diagnostically to detect agents (e.g. antibodies) which bind specifically to them. They may also be used to produce neutralising agents, for example antibodies, which neutralise the toxin. Agents which bind the epitopes may be used both therapeutically and diagnostically.

According to the present invention there is provided an epitope of a Shigella-like toxin, having a sequence selected from any one of the group of SEQ ID NOs: 1–7. The epitope may have a sequence selected from either one of SEQ ID NOs: 1 and 3. The epitopes of the present invention may also be described as peptides carrying epitopes of a Shigella-like toxin.

The epitopes of SEQ ID NOs: 1–7 have not been previously identified, nor have they been suggested. Although the sequences of various SLTs are known, specific epitopes are not.

The epitopes of the present invention are also considered to encompass analogues of the epitopes. Analogues may be readily produced, for example in the form of mimotopes (Geysen, H. M. et al., 1987, Journal of Immunological Methods, 102: 259–274; Geysen, H. M. et al.,1988, J. Mol. Recognit., 1(1):32–41; Jung, G. and Beck-Sickinger, A. G., 1992, Angew. Chem. Int. Ed. Eng., 31: 367–486) using commercially available mimotope design technology.

The Shigella-like toxin may be that from an *E. coli.* It may be that from an *E. coli* O157 selected from the group of O157:H7, O157:$H^-$ and O26:H11. Alternatively, the Shigella-like toxin may be selected from the group of that of *Shigella sonnei, Shigella boydii, Shigella flexneri*, and *Shigella dysenteriae.*

The epitope may be for use in a method of treatment or diagnosis of the human or animal body.

The epitope may for example be for use as an immunogen, for example a vaccine.

Also provided according to the present invention are binding agents specific against an epitope according to the present invention. Binding agents include any molecule which is capable of recognising an epitope according to the present invention. For example a binding agent may be an antibody or an antigen binding fragment thereof.

Antibodies are well known (Harlow, E. and Lane, D., "Antibodies—A Laboratory Manual", Cold Spring Harbor Laboratory, Cold Spring Harbor Press, New York, 1988). The antibody may be a whole antibody or an antigen binding fragment thereof and may in general belong to any immunoglobulin class. Thus, for example, it may be an IgM or an IgG antibody. The antibody or fragment may be of animal, for example, mammalian origin and may be for example of murine, rat, sheep or human origin. It may be a natural antibody or a fragment thereof, or, if desired, a recombinant antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in, for example, EP 239400); (2) recombinant antibodies or fragments wherein non-Fv sequences have been substituted by non-Fv sequences from other, different antibodies (as described in, for example, EP 171469, 173494 and 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, PCT/GB88/00730 and PCT/GB88/00729).

The antibody or antibody fragment may be of polyclonal or monoclonal origin. It may be specific for at least one epitope.

Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described, for example, in PCT/GB88/0747).

The antibodies according to the invention may be prepared using well-known immunological techniques. Thus, for example, any suitable host may be injected with the protein and the serum collected to yield the desired polyclonal antibody after appropriate purification and/or concentration (for example by affinity chromatography using the immobilised protein as the affinity medium). Alternatively splenocytes or lymphocytes may be recovered from the protein-injected host and immortalised using for example the method of Kohler et al. (1976, Eur. J. Immunol., 6: 511), the resulting cells being segregated to obtain a single genetic line producing monoclonal antibodies. Antibody fragments may be produced using conventional techniques, for example, by enzymatic digestion with pepsin or papain. Where it is desired to produce recombinant antibodies according to the invention these may be produced using, for example, the methods described in EP 171469, EP 173494, EP 194276 and EP 239400.

Antibodies according to the invention may be labelled with a detectable label or may be conjugated with an effector molecule, for example a drug eg. an antibacterial agent or a toxin or an enzyme, using conventional procedures and the invention extends to such labelled antibodies or antibody conjugates. Thus a binding agent according to the present invention may not only bind to the Shigella-like toxin but may also neutralise it (i.e. inhibit its cytotoxicity).

Binding agents according to the present invention may be for use in a method of treatment or diagnosis of the human or aniomal body.

Also provided according to the present invention is the use of an epitope or binding agent according to the present invention in the manufacture of a medicament for the treatment of a condition resulting from a Shigella-like toxin. Also provided is a method of manufacture of a medicament for the treatment of a condition resulting from a Shigella-like toxin, comprising the use of an epitope or binding agent according to the present invention.

Thus the present invention provides epitopes of Shigella-like toxins, which may be used therapeutically or diagnostically, together with binding agents derived therefrom which themselves may be used both diagnostically or therapeutically.

Also provided according to the present invention is a diagnostic test method for a Shigella-like toxin displaying an epitope according to the present invention comprising the steps of:

i) reacting a binding agent according to the present invention with a sample
ii) detecting a binding agent-epitope binding reaction; and
iii) correlating the detection of the binding reaction with the presence of the Shigella-like toxin.

The binding agent may for exampe be an antibody, and the diagnostic test method comprise the steps of:

i) reacting an antibody according to the present invention with a sample;
ii) detecting an antibody-antigen binding reaction; and
iii) correlating the detection of the binding reaction with the presence of the Shigella-like toxin.

Where the binding agent is an antibody or antigen binding fragment thereof, the epitopes may be regarded as being antigens.

Also provided is a diagnostic test method for antibody specific against a Shigella-like toxin comprising the steps of:

i) reacting an epitope according to the present invention with a sample;
ii) detecting an antibody-antigen binding reaction; and
iii) correlating the detection of the antibody-antigen binding reaction with the presence of antibody specific against a Shigella-like toxin.

The sample may be from a patient, for example a serum sample or a peritoneal dialysate, although any other sample which may contain, or which might be expected to contain, Shigella-like toxins may of course be used.

Also provided according to another aspect of the present invention is a diagnostic test kit for performing a diagnostic test method according to the present invention. Diagnostic test kits are well known and may for example include dip-stick tests according to WO 88/08534. The test kit may include instructions for its use in a diagnostic test method according to the present invention.

Also provided according to the present invention is a method of treatment or diagnosis of the human or animal body comprising the use of an epitope or binding agent according to the present invention.

Medicaments and methods of treatment according to the present invention will be readily apparent to one skilled in the art. Medicaments may be prepared using pharmaceutically acceptable carriers, diluents or excipients (Remington's Pharmaceutical Sciences and US Pharmacopeia (1984) Mack Publishing Company., Easton, Pa., USA). The medicaments and methods of treatment may be effected using a pharmaceutically effective amount of the epitope or binding agent. Appropriate dosages will be readily apparent to one skilled in the art and may be readily determined, for example by means of dose-response experiments.

The invention will be further apparent from the following description which shows, by way of example only, epitopes according to the present invention, and peptides carrying same.

EXPERIMENTAL

Sera was available from various patients infected with *E. coli* O157:H7 (1996, BMJ, 313: 1424) at various stages of infection. The sera were epitope mapped (below) and comparisons made to identify epitopes within the derived amino acid sequence of subunit A of the SLT (Verotoxin, Meyer, T. et al., 1992, Zbl. Bakt., 276: 176–188) expressed by the bacterium.

Epitope Mapping

A series of overlapping nonapeptides covering the derived amino acid sequence was synthesised on polyurethane pins with reagents from an epitope scanning kit (Cambridge Research biochemicals, Cambridge, UK) as described previously by Geysen et al. (1987, Journal of Immunological Methods, 102: 259–274). Peptide 1 (well 1) consisted of residues 1 to 9 (SEQ ID NO: 8), peptide 2 (well 2) consisted of residues 2 to 10 (SEQ ID NO: 9) etc. This was performed for the verotoxin derived from the *E. coli* O157. The reactivity of each clone with patient sera (diluted 1 in 1000) was determined for IgG by ELISA. Data were expressed as A405 after 30 minutes of incubation.

Paired sera were available from 3 patients at early (day 3 of infection) and late (6 weeks post-infection) stages of infection. A mean for each well was calculated for both the early and late sera by combining the results from the three patients. The late sera results were subtracted from the early sera results. Areas where at least three consecutive wells were positive (at least 0.19) were deemed as defining an epitope. Secondly a single serum (taken at day 3 of infection) was examined from a patient who later died due to the infection. The values obtained were subtracted from the mean values previously described for the early sera of surviving patients. Areas where at least three consecutive wells were positive (at least 0.19) were deemed as defining an epitope.

This resulted in the identification of seven epitopes (SEQ ID NOs: 1–7 respectively). The seven epitopes described fulfilled at least one of these criteria. Epitopes 1 and 3 fulfilled both criteria (Table 1)

TABLE 1

| Epitope SEQ ID NO: | Well Numbers | Mean of 3 paired sera (Early-Late) | Early-Negative (single sera) |
|---|---|---|---|
| 2 | 82 | 0.202 | 0.254 |
| | 83 | 0.241 | 0.338 |
| | 84 | 0.331 | 0.224 |
| 4 | 139 | 0.234 | 0.196 |
| | 140 | 0.192 | 0.193 |
| | 141 | 0.205 | 0.219 |

Further epitope mapping was performed as follows using the same series of overlapping nonapeptides as before.

Collection of Patients' Sera

Six sera were obtained from patients who were confirmed as having HUS (haemolytic uraemic syndrome). Three sera were obtained from patients who had *E. coli* O157 isolated from a stool sample who had not progressed to HUS, and one serum was obtained as a negative control from a leukaemic patient. All sera were measured for IgG.

Results

By addition of the mean absorbance values the six sera from the patients with HUS and the three sera from the patients with a positive faecal sample and after subtraction of the negative control, epitopes were defined as a consecutive series of 3 or more wells which had an absorbance of greater than a cut-off of 0.5. A total of 7 epitopes were identified by this criterion. The epitope sequence and the peptide number at which they occur are given in Table 4. No epitopes were shown in the B subunit.

Additional experiments were undertaken as follows:

Materials and Methods

Five areas were synthesised as short peptides by a BT 7400 multiple peptide synthesiser (Biotech Instruments, Luton, UK). These were used in the indirect ELISA. The peptide number and amino acid sequences were as follows: Peptides 1–5—SEQ ID NOs: 10–14 respectively. Peptide 1 carried the epitope of SEQ ID NO: 2. Peptide 2 carried the epitope of SEQ ID NO: 3. Peptide 3 carried the epitope of SEQ ID NO: 4. Peptides 4 and 5 carried the epitope of SEQID NO: 5.

A total of 25 sera with different clinical histories, 3 sera from patients with no evidence of *E. coli* O157 infection, 20 sera from patients who had been hospitalised with a diagnosis of haemolytic uraemic syndrome and a positive culture from faeces of *E. coli* O157 and a second serum from 2 patients, taken four weeks later, who had recovered from *E. coli* O157 related disease. The paired sera were numbered 1 and 2 and 3 and 4 respectively. The control sera were numbers 23–25 (Table 2).

Indirect ELISA

By a simple adsorbtion of peptides to a microtitre plate the following procedure was performed for each peptide. The peptide was dissolved in 2 ml of 0.01 M phosphate buffer saline (PBS), pH 7.2 and diluted to a concentration of 10 μg/ml (1/100) in the same buffer.

(1) 150 μl aliquots of peptide (10 μg/ml in 0.01M PBS) were pipetted into the wells of a Falcon 3912 microassay plate and were incubated overnight at 4° C.

(2) The unbound peptide was removed by washing four times (4×10 minutes) with 0.05% Tween 20 in 0.01 M PBS (pH 7.2).

(3) The plates were blocked with 2% skimmed milk-10% FCS in 0.01M PBS for 1 hour at 37° C.

(4) The plates were washed four times (4×10 minutes) with 0.05% Tween 20 in 0.01 M PBS and the serum under investigation was added (1/100 dilution in blocking solution) into the wells of micro assay plate (three wells used for each serum) and incubated for 2 hours at 37° C.

(5) The plates were washed four times (4×10 minutes) with 0.05% Tween 20 in 0.01 M PBS and secondary antibody, anti-human IgM (or IgG) peroxidase conjugate (1/1000 dilution in blocking solution) was added and incubation proceeded for 1 hour at 37° C.

(6) The plates were washed four times (4×10 minutes) with 0.05% Tween 20 in 0.01 M PBS, followed by a ether washing with 0.01 M PBS. The plate was then incubated for 45 minutes at room temperature with agitation in 0.5 mg/ml of freshly prepared 2,2 Azino-bis[3-ethylbenzthiazoline-6-sulfonic acid]diammonium (ABTS tablets) in pH 4.0 citrate buffer with 0.01% (w/v) hydrogen peroxide.

(7) Control wells were used in each plate. The three wells having ABTS solution only and three wells having ABTS solution plus anti-human IgG or IgM horseradish peroxidase conjugate only were used.

(8) Optical density (OD) measurements were made with an ELISA plate reader (Titertek-Multiscan) at a wavelength of 405 nm.

(9) The average readings for each of three wells per patient's serum was determined.

Results

These are summarised in Table 2. At a cut off OD of 0.2 for IgM and 0.3 for IgG, peptide 4 was the most immunoreactive, although one control serum was positive for IgM. When the cut off OD was increased to 0.25 (IgM) and 0.35 (IgG), peptide 5 was the most immunoreactive (Table 3).

With the more sensitive cut off points and by defining a serum positive if either IgM and/or IgG was positive then peptide 1 was positive in 4 cases, peptide 2 in 6 cases, peptide 3 in 12 cases, peptide 4 in 16 cases and peptide 5 in 9 cases. The sera from cases 6, 7 and 15 were negative with all five peptides. Paired sera from Case 1 showed an increase in IgM against peptides 1, 3, 4 and 5 whilst the levels of IgG remained constant. Paired sera from Case 2 showed an increase in IgM against peptides 1, 2, 3 and 4 and IgG against peptides 2 and 3.

Conclusion

Antibody was produced against peptides derived from the toxin of *E. coli* O157. This confirmed the results of the epitope map and that these areas within the molecule are targets for antibody therapy. Peptide 4 and peptide 5 contained the same epitope (SEQ ID NO: 5) but in peptide 4 this was linked to the corresponding sequence from *E. coli* O157 whilst in peptide 5 this was the equivalent from the holotoxin of *Shigella dysenteriae* (Fraser et al., Nature Structural Biology, 1(1): 59–64). The reduction in immunogenicity with the sequence derived from *S. dysenteriae* underlines the specificity of the reaction against the *E. coli* O157 derived epitope.

TABLE 2

Details of the ODS of sera against each peptide

| Serum | Case | Peptide Number 1 | | 2 | | 3 | | 4 | | 5 | |
|---|---|---|---|---|---|---|---|---|---|---|---|
| No. | No. | IgM | IgG | IgM | IgG | IgM | IgG | IgM | IgG | IgM | IgG |
| 1 | 1 | 0.194 | 0.236 | 0.209 | 0.309 | 0.202 | 0.255 | 0.243 | 0.341 | 0.181 | 0.205 |
| 2 | | 0.283 | 0.218 | 0.215 | 0.303 | 0.256 | 0.249 | 0.277 | 0.264 | 0.230 | 0.185 |
| 3 | 2 | 0.188 | 0.231 | 0.171 | 0.297 | 0.215 | 0.190 | 0.213 | 0.717 | 0.136 | 0.180 |
| 4 | | 0.251 | 0.274 | 0.200 | 0.379 | 0.307 | 0.334 | 0.324 | 0.272 | 0.173 | 0.150 |
| 5 | 3 | 0.173 | 0.202 | 0.176 | 0.272 | 0.179 | 0.219 | 0.208 | 0.312 | 0.157 | 0.170 |
| 6 | 4 | 0.189 | 0.193 | 0.174 | 0.277 | 0.181 | 0.228 | 0.193 | 0.258 | 0.110 | 0.120 |
| 7 | 5 | 0.167 | 0.188 | 0.171 | 0.254 | 0.190 | 0.172 | 0.193 | 0.197 | 0.160 | 0.230 |
| 8 | 6 | 0.189 | 0.327 | 0.171 | 0.358 | 0.188 | 0.31 | 0.193 | 0.306 | 0.152 | 0.346 |
| 9 | 7 | 0.196 | 0.209 | 0.190 | 0.280 | 0.198 | 0.257 | 0.236 | 0.300 | 0.241 | 0.301 |
| 10 | 8 | 0.191 | 0.166 | 0.195 | 0.277 | 0.213 | 0.18 | 0.226 | 0.236 | 0.213 | 0.244 |
| 11 | 9 | 0.161 | 0.171 | 0.175 | 0.229 | 0.207 | 0.177 | 0.208 | 0.40 | 0.146 | 0.175 |
| 12 | 10 | 0.241 | 0.227 | 0.188 | 0.281 | 0.237 | 0.252 | 0.263 | 0.239 | 0.269 | 0.423 |
| 13 | 11 | 0.173 | 0.209 | 0.183 | 0.267 | 0.212 | 0.252 | 0.201 | 0.327 | 0.321 | 0.300 |
| 14 | 12 | 0.178 | 0.146 | 0.175 | 0.304 | 0.217 | 0.228 | 0.219 | 0.262 | 0.187 | 0.511 |
| 15 | 13 | 0.149 | 0.206 | 0.163 | 0.212 | 0.185 | 0.192 | 0.184 | 0.230 | 0.162 | 0.21 |
| 16 | 14 | 0.189 | 0.190 | 0.170 | 0.241 | 0.214 | 0.312 | 0.215 | 0.225 | 0.168 | 0.255 |
| 17 | 15 | 0.164 | 0.184 | 0.170 | 0.265 | 0.186 | 0.205 | 0.190 | 0.316 | 0.159 | 0.21 |
| 18 | 16 | 0.18 | 0.188 | 0.177 | 0.270 | 0.198 | 0.213 | 0.209 | 0.255 | 0.178 | 0.27 |
| 19 | 17 | 0.169 | 0.181 | 0.177 | 0.206 | 0.242 | 0.236 | 0.230 | 0.219 | 0.255 | 0.170 |
| 20 | 18 | 0.160 | 0.180 | 0.170 | 0.322 | 0.170 | 0.306 | 0.185 | 0.223 | 0.13 | 0.355 |
| 21 | 19 | 0.171 | 0.257 | 0.175 | 0.309 | 0.204 | 0.241 | 0.196 | 0.396 | 0.185 | 0.18 |
| 22 | 20 | 0.162 | 0.209 | 0.167 | 0.274 | 0.198 | 0.244 | 0.208 | 0.277 | 0.163 | 0.18 |
| 23 | Control | 0.173 | 0.239 | 0.165 | 0.252 | 0.198 | 0.263 | 0.196 | 0.241 | 0.14 | 0.32 |
| 24 | Control | 0.181 | 0.254 | 0.170 | 0.283 | 0.198 | 0.294 | 0.212 | 0.259 | 0.129 | 0.19 |
| 25 | Control | 0.181 | 0.204 | 0.170 | 0.277 | 0.191 | 0.237 | 0.189 | 0.242 | 0.135 | 0.15 |

TABLE 3

Correlation of the cut-off points with the number of positive sera from the 20 cases examined.

| Number of | 1 | | 2 | | 3 | | 4 | | 5 | |
|---|---|---|---|---|---|---|---|---|---|---|
| positive sera | IgM | IgG | IgM | IgG | IgM | IgG | IgM[a] | IgG | IgM | IgG[a] |
| IgM > 0.2 IgG > 0.3 | 3 | 1 | 2 | 6 | 10 | 4 | 12 | 7 | 6 | 5 |
| IgM > 0.25 IgG > 0.35 | 2 | 0 | 0 | 2 | 2 | 0 | 3 | 1 | 3 | 3 |

[a]single control serum was also positive

TABLE 4

| Epitopes identified when the absorbance values of the negative control serum is subtracted from the positive sera. | | |
|---|---|---|
| Epitope | Peptide Number | Absorbance at 405 nm |
| 1 | 76 | 0.525 |
| | 77 | 0.650 |
| | 78 | 0.516 |
| 2 | 82 | 0.546 |
| | 83 | 0.693 |
| | 84 | 0.744 |
| | 85 | 0.595 |
| | 86 | 0.663 |
| 3 | 134 | 0.500 |
| | 135 | 0.528 |
| | 136 | 0.573 |
| | 137 | 0.525 |
| | 138 | 0.353 |
| | 139 | 0.576 |
| | 140 | 0.445 |
| | 141 | 0.598 |

TABLE 4-continued

| Epitopes identified when the absorbance values of the negative control serum is subtracted from the positive sera. | | |
|---|---|---|
| Epitope | Peptide Number | Absorbance at 405 nm |
| 4 | 174 | 0.677 |
| | 175 | 0.504 |
| | 176 | 0.626 |
| | 177 | 0.591 |
| | 178 | 0.596 |
| | 179 | 0.546 |
| 5 | 189 | 0.501 |
| | 190 | 0.606 |
| | 191 | 0.568 |
| | 192 | 0.508 |
| | 193 | 0.523 |
| | 194 | 0.704 |
| | 195 | 0.394 |
| | 196 | 0.522 |
| 6 | 238 | 0.612 |
| | 239 | 0.525 |
| | 240 | 0.557 |
| | 241 | 0.529 |
| 7 | 266 | 0.505 |
| | 267 | 0.503 |
| | 268 | 0.776 |

SEQUENCE LISTING

```
<160> NUMBER OF SEQ ID NOS:  14

<210> SEQ ID NO 1
<211> LENGTH: 7
<212> TYPE: PRT
<213> ORGANISM: Escherichia coli

<400> SEQUENCE: 1

Gly Leu Asp Val Tyr Gln Ala
  1               5


<210> SEQ ID NO 2
<211> LENGTH: 6
<212> TYPE: PRT
<213> ORGANISM: Escherichia coli

<400> SEQUENCE: 2

Arg Phe Asp His Leu Arg
  1               5


<210> SEQ ID NO 3
<211> LENGTH: 7
<212> TYPE: PRT
<213> ORGANISM: Escherichia coli

<400> SEQUENCE: 3

Arg Val Ala Ala Leu Glu Arg
  1               5
```

-continued

```
<210> SEQ ID NO 4
<211> LENGTH: 5
<212> TYPE: PRT
<213> ORGANISM: Escherichia coli

<400> SEQUENCE: 4

Arg Ala Val Leu Arg
  1               5


<210> SEQ ID NO 5
<211> LENGTH: 7
<212> TYPE: PRT
<213> ORGANISM: Escherichia coli

<400> SEQUENCE: 5

Arg Gln Ile Gln Arg Glu Phe
  1               5


<210> SEQ ID NO 6
<211> LENGTH: 7
<212> TYPE: PRT
<213> ORGANISM: Escherichia coli

<400> SEQUENCE: 6

Trp Gly Arg Ile Ser Asn Val
  1               5


<210> SEQ ID NO 7
<211> LENGTH: 7
<212> TYPE: PRT
<213> ORGANISM: Escherichia coli

<400> SEQUENCE: 7

Ala Arg Ser Val Arg Ala Val
  1               5


<210> SEQ ID NO 8
<211> LENGTH: 9
<212> TYPE: PRT
<213> ORGANISM: Escherichia coli

<400> SEQUENCE: 8

Met Lys Cys Ile Leu Phe Lys Trp Val
  1               5


<210> SEQ ID NO 9
<211> LENGTH: 9
<212> TYPE: PRT
<213> ORGANISM: Escherichia coli

<400> SEQUENCE: 9

Lys Cys Ile Leu Phe Lys Trp Val Leu
  1               5


<210> SEQ ID NO 10
<211> LENGTH: 15
<212> TYPE: PRT
<213> ORGANISM: Escherichia coli

<400> SEQUENCE: 10

Asp Val Tyr Gln Ala Arg Phe Asp His Leu A rg Leu Ile Ile Glu
  1               5                   10                  15
```

-continued

```
<210> SEQ ID NO 11
<211> LENGTH: 16
<212> TYPE: PRT
<213> ORGANISM: Escherichia coli

<400> SEQUENCE: 11

Thr Thr Leu Gln Arg Val Ala Ala Leu Glu A rg Ser Ser Gly His Gln
  1               5                  10                  15


<210> SEQ ID NO 12
<211> LENGTH: 15
<212> TYPE: PRT
<213> ORGANISM: Escherichia coli

<400> SEQUENCE: 12

Thr Arg Asp Ala Ser Arg Ala Val Leu Arg P he Val Thr Val Thr
  1               5                  10                  15


<210> SEQ ID NO 13
<211> LENGTH: 15
<212> TYPE: PRT
<213> ORGANISM: Escherichia coli

<400> SEQUENCE: 13

Leu Arg Phe Arg Gly Ile Gln Arg Glu Phe A rg Gln Ala Leu Ser
  1               5                  10                  15


<210> SEQ ID NO 14
<211> LENGTH: 15
<212> TYPE: PRT
<213> ORGANISM: Artificial Sequence
<220> FEATURE:
<223> OTHER INFORMATION: Description of Artificial  Sequence: Epitope
      linked to Shigella dysenteriae holo toxin sequence

<400> SEQUENCE: 14

Ala Glu Ala Leu Arg Phe Arg Gln Ile Gln A rg Glu Phe Arg Gln
  1               5                  10                  15
```

What is claimed is:

1. An isolated peptide of a Shigella-like toxin, wherein said peptide carries the epitope consisting of SEQ ID NO: 5, wherein said peptide is selected from the group consisting of SEQ ID NOs 5, 13 and 14.

2. An isolated peptide according to claim 1, the Shigella-like toxin being that from an *E. coli.*

3. The isolated peptide according to claim 2, the Shigella-like toxin being that from an *E. coli* O157 selected from the group of O157:H7, O157:H– and O26:H11.

4. The isolated peptide according to claim 1, the Shigella-like toxin being selected from the group of that of *Shigella sonnei, Shigella Boydii, Shigella flexneri*, and *Shigella dysenteriae.*

5. A composition comprising an isolated peptide according to claim 1 and a pharmaceutically acceptable carrier, diluent or excipient.

6. A composition according to claim 5 comprising a pharmaceutically effective amount of said isolated peptide.

* * * * *

UNITED STATES PATENT AND TRADEMARK OFFICE

CERTIFICATE OF CORRECTION

PATENT NO. : 6,410,024 B1
DATED : June 25, 2002
INVENTOR(S) : Burnie et al.

It is certified that error appears in the above-identified patent and that said Letters Patent is hereby corrected as shown below:

Title page,
Item [73], Assignee, please correct the spelling of the Assignee to read
-- NeuTec Pharma PLC --.

Signed and Sealed this

Twentieth Day of May, 2003

JAMES E. ROGAN
*Director of the United States Patent and Trademark Office*